(12) United States Patent
Yavitz

(10) Patent No.: US 6,247,473 B1
(45) Date of Patent: Jun. 19, 2001

(54) SYSTEM AND METHOD FOR TESTING THE NEUROPROTECTIVE OR NEUROREGENERATIVE EFFECTS OF DRUGS

(75) Inventor: Edward Q. Yavitz, Rockford, IL (US)

(73) Assignee: Third Millenium Trust, Scottsdale, AZ (US)

( * ) Notice: Subject to any disclaimer, the term of this patent is extended or adjusted under 35 U.S.C. 154(b) by 0 days.

(21) Appl. No.: 09/252,579

(22) Filed: Feb. 18, 1999

(51) Int. Cl.[7] ................................................ A61B 19/00
(52) U.S. Cl. ............................................................ 128/898
(58) Field of Search ............................................... 128/898

(56) References Cited

U.S. PATENT DOCUMENTS 5,523,301  6/1996  Amon et al. ...................... 514/236.2
5,856,329  1/1999  Wheeler et al. ...................... 514/255

OTHER PUBLICATIONS

Robert David, "Changing therapeutic paradigms in glaucoma management" 1998 Ashley Publications Ltd. ISSN 1354–3784; pp. 1063, 1074–1076.

Primary Examiner—Dinh X. Nguyen
(74) Attorney, Agent, or Firm—Fletcher, Yoder & Van Someren

(57) ABSTRACT

A system and method for testing neuroregenerative and neuroprotective effects of specific substances on a human central nervous system. The method utilizes a standard ophthalmological procedure in which measurable but clinically insignificant damage occurs to the nerve fiber layer in a human eye. The method includes comparing the protection or regeneration of the nerve fiber layer in a patient provided with a test treatment versus a placebo treatment. Because the eyes are the only bilateral or duplicated manifestation of the human central nervous system, each human subject can act as his or her own control subject.

19 Claims, 2 Drawing Sheets

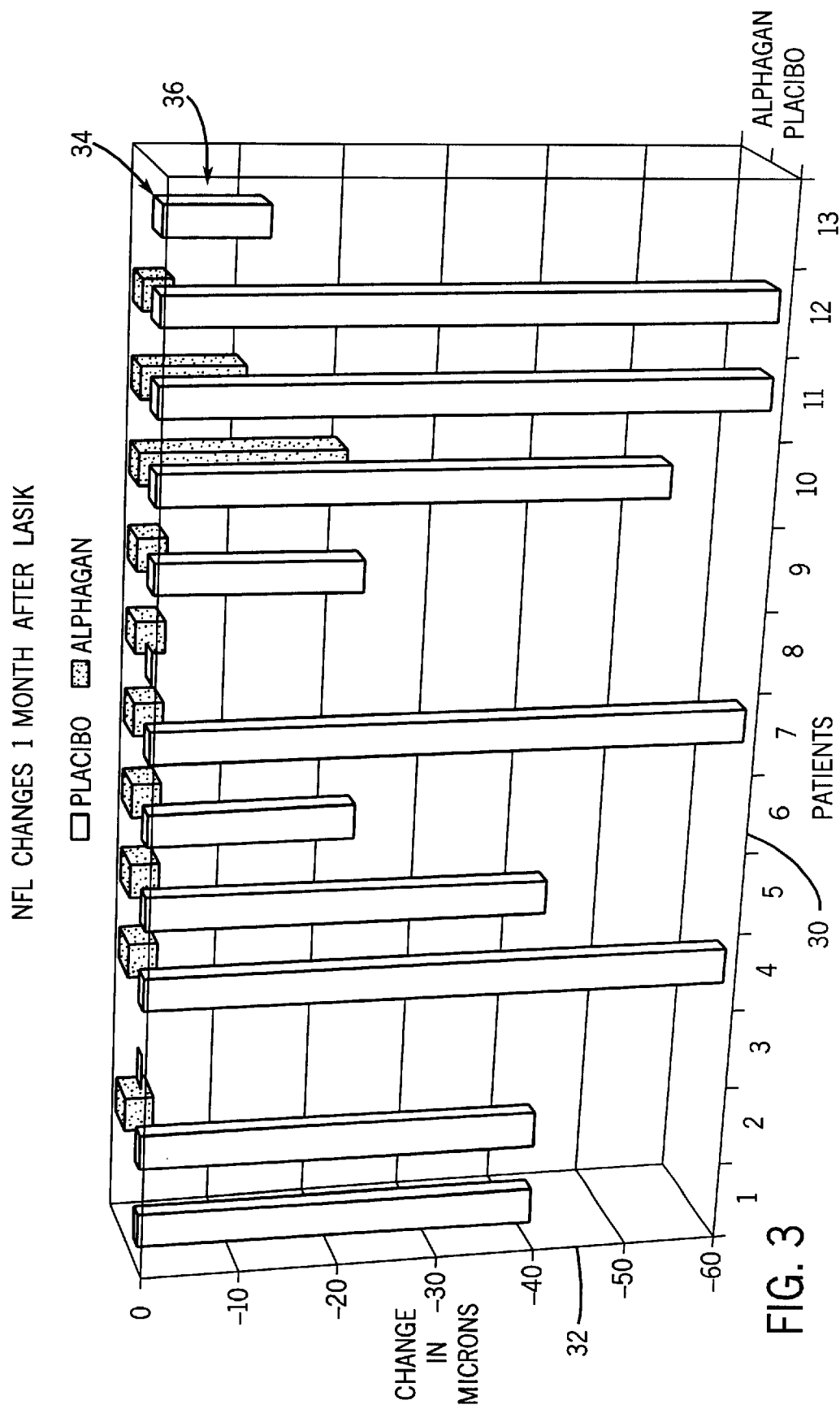

SYSTEM AND METHOD FOR TESTING THE NEUROPROTECTIVE OR NEUROREGENERATIVE EFFECTS OF DRUGS

FIELD OF THE INVENTION

The present invention relates generally to a system and method for testing neurological treatments, and particularly to the testing of neuroprotective and neuroregenerative effects of various drugs on humans.

BACKGROUND OF THE INVENTION

There has been substantial research in the area of preventing or repairing damage to the central nervous system. Certain drugs, such as brimonidine and various beta-adrenergic blocking agents, have been accepted as neuroprotective drugs that can protect the central nervous system from acute ischemia and crush trauma in humans. Evidence now shows that at least some of the drugs can stabilize, reinforce or even regenerate neurotubules within central or peripheral neurons of a human nervous system to prevent or regenerate damage caused by, for instance, direct crush injury.

Research and testing of such neuroprotective and/or neuroregenerative drugs can be problematic due to the difficulty in performing actual tests prospectively on human subjects. Traditionally, research has been done on animals, but this has limited the ability of scientists to develop new drugs, because results in animals do not always correlate with results in humans.

The ability to test neuroprotective or neuroregenerative drugs on humans would provide researchers with an additional tool that would accelerate the development of drugs for a wide variety of neurological problems. For example, research is being done and there is hope for drugs that will protect and repair nerves damaged in, for example, compression fractures of the spine. The ability to test such drugs on human subjects would also aid in the research into drugs that could negate the neurological damage due to strokes or neuralapostosis in which nerves send self-destruct signals subsequent to being damaged. There is a great need for drugs which are able to slow or stop such neurological damage.

It would be advantageous to determine a common procedure or occurrence that produces readily measurable but clinically insignificant damage to the human central nervous system to facilitate testing of such drugs or other treatments.

SUMMARY OF THE INVENTION

The present invention features a method for testing the neuroprotective or neuroregenerative effects of a substance on a human central nervous system without clinically significant damage to neural tissue. The method includes creating a vacuum on an external surface of an eye of a human. The method further includes measuring the extent of loss to central nervous tissue of the eye due to the vacuum.

Either before and/or after creation of the vacuum, the human is treated with a test substance. After a predetermined period, loss of central nervous tissue due to the vacuum is measured to determine the effect of the test substance. The results are then compared to a control.

According to another aspect of the invention, a method is provided for testing neuroprotective or neuroregenerative effects of a treatment on nerve tissue of a human. The method includes causing measurable but clinically insignificant damage to nerve tissue of a human and treating the human. The treatment can either be before and/or after the creation of the clinically insignificant nerve tissue damage. Subsequently, the depletion of nerve tissue is measured after a designated period following creation of the clinically insignificant nerve tissue damage and the treatment.

According to another aspect of the invention, a method is provided for testing neuroregenerative or neuroprotective effects on a human central nervous system. The method includes producing measurable but clinically insignificant damage to a human central nervous system in a statistically significant number of human subjects. The method also includes producing measurable but clinically insignificant damage to a control human central nervous system in a statistically significant number of human control subjects. The method also includes treating the statistically significant number of human subjects with a test substance, and comparing human central nervous system damage in the statistically significant number of human subjects with the statistically significant number of human control subjects. By this method, the neuroprotective or neuroregenerative effects of the test substance may be determined.

BRIEF DESCRIPTION OF THE DRAWINGS

The invention will hereafter be described with reference to the accompanying drawings, wherein like reference numerals denote like elements, and:

FIG. 3 is a bar chart illustrating changes in nerve fiber layer thickness of patients who receive either a neuroprotective treatment or a placebo treatment prior to initiation of an ophthalmological procedure utilizing a microkeratome to raise the intraocular pressure in the patients' eyes.

DETAILED DESCRIPTION OF THE PREFERRED EMBODIMENTS

Figure 1:
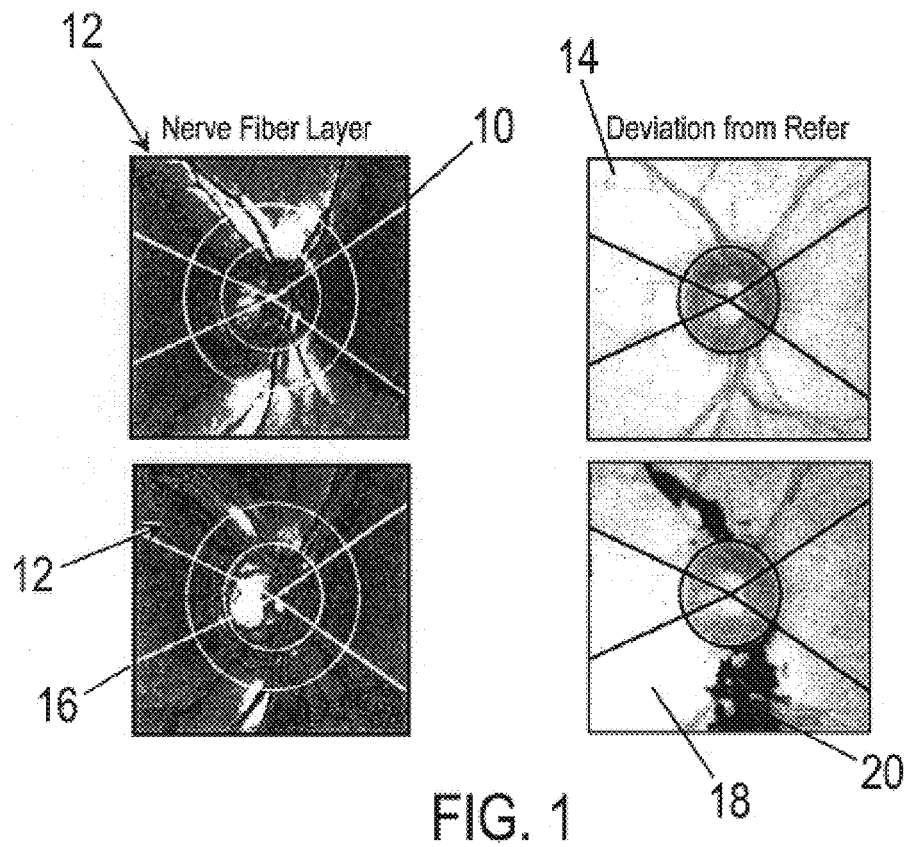
FIG. 1 is a representation of a nerve fiber layer analysis in an eye of a human subject before and after application of a microkeratome to show the effect of placebo drops applied to the eye.

In testing the neuroprotective and/or neuroregenerative effects of a given substance on human central nervous systems, it is desirable to test proposed substances on a statistically significant number of human subjects. As in any scientific study, a sufficient number of human subjects tested with a given substance are compared with a statistically significant control group in an attempt to accurately measure the neuroprotective or neuroregenerative effects of the given substance. Heretofore, the use of humans in testing such drugs has been problematic due to the need to administer the given substance or treatment prior to or subsequent to damage inflicted on the human central nervous system.

However, an original discovery made by the inventor is that during certain routine ophthalmological procedures, readily measurable but clinically insignificant damage occurs to the human central nervous system. By way of specific example, LASIK (laser in-situ keratomileusis) procedures cause an acute ischemia or crush injury that damages the neurotubules within the retinal ganglion cells and the nerve fiber layer.

The damage causes a measurable decrease in the thickness of the nerve fiber layer. However, the damage is clinically insignificant in that it produces no noticeable lasting effects for the patient undergoing the LASIK procedure. Accordingly, the tangential damage to the human central nervous system that occurs during a routine medical procedure provides an opportunity for the prospective testing of neuroprotective and neuroregenerative treatments.

Furthermore, the eyes are the only bilateral or duplicated manifestation of the human central nervous system. All other duplicated nerves are peripheral, and thus are unsuitable for direct measurement of nerve loss in the brain. The eyes, therefore, are advantageous for testing the neuroprotective or neuroregenerative effects of substances on the human central nervous system. Each human subject potentially can act not only as a human test subject but also as a human control subject when the human central nervous system is tested bilaterally and simultaneously. Effectively, one eye of a human subject can be used as the test treatment site while the other eye is used as the control to which, for example, a placebo is administered.

To understand one acceptable procedure for the creation of readily measurable but clinically insignificant damage to the human nervous system, it is necessary to understand a conventional LASIK procedure, as explained below. However, this should not be construed as limiting the methodology described herein to use solely in conjunction with LASIK procedures. For example, certain portions of the LASIK procedure could be replicated or other procedures could be used to achieve the resultant clinically insignificant damage to the human central nervous system.

In a typical LASIK procedure, the subjects eyelids are cleaned with Betadine® or another appropriate substance. Following cleaning, this area of the eye is irrigated with sterile water or saline. After drying the area, the lashes and lid margin are draped, and an adjustable eye speculum is utilized to expand the eyelids and expose the eye. Before or during this procedure, an appropriate anesthesia is applied.

Following preparation of the human subject, a microkeratome, such as the FlapMaker™ microkeratome system is removed from its sterile packaging. The microkeratome is inspected and connected to the appropriate cables and tubing, as required by the particular brand of microkeratome and as known by those of ordinary skill in the art. Once the microkeratome is prepared for operation, one or two drops of filtered, balanced salt solution are placed on the cornea, and the cornea is prepared by making reference marks to ensure proper realignment of the corneal flap to be created during the procedure. The microkeratome is then visually centered over the patient's cornea and placed on an eye of the human subject. Sometimes, the microkeratome is de-centered a small amount. The microkeratome is pressed against the subject's eye to create a "seat" with the cornea. The microkeratome actually includes a suction ring that seats with the cornea and allows suction to be applied to the eye.

After placement, the microkeratome is connected to a suction pump via an appropriate tube, and suction is applied to the eye. This suction creates an intraocular pressure (IOP) that is typically increased to at least 65 mm Hg as measured by a pneumotonometer, such as the Mentor® Model 30 Classic Pneumotonometer. More typically, an intraocular pressure of at least 80 mm Hg is applied.

The suction is applied and the intraocular pressure is created to present a firm corneal surface that can be cut by a blade of the microkeratome. During this period of increased intraocular pressure, an appropriate flap may be cut with the assistance of the microkeratome. After the flap is created, the vacuum is released, and the flap is folded back to expose the corneal tissue. This corneal tissue is exposed to ultraviolet light and high energy pulses from an excimer laser used to reshape the internal cornea with great accuracy. By adjusting the pattern of the laser beam, relatively high levels of nearsightedness and moderate levels of farsightedness and astigmatism may be treated.

Following reshaping of the internal cornea, the flap is replaced in its original position. The flap is readily able to bond to the surrounding corneal tissue, and the healing process tends to be rapid.

During this procedure, and specifically during the period in which a suction is applied to the eye to raise the intraocular pressure, it has been determined that readily measurable but clinically insignificant damage occurs to the human central nervous system in the form of a thinner nerve fiber layer. (It should be noted that the actual thinning of the nerve fiber layer is contrary to conventional wisdom and previous studies, such as a study by Ming Wang, M.D. Ph.D. of Vanderbilt University Medical Center reported in July of 1998.)

Measurable nerve loss has been proved by the present inventor with the aid of a GDx® Nerve Fiber Layer Analyzer available from Laser Diagnostic, Inc. Such nerve fiber analyzers are extremely accurate and generally used to assist in the early detection and treatment of glaucoma. However, the accuracy of GDx® NFL analyzer, which has a precision to less than seven millionths of a meter, permits measurement of minute amounts of damage caused to the nerve fiber layer of the human central nervous system. Such minute amounts of damage occur as a result of the increase in intraocular pressure during LASIK procedures.

Accordingly, the measurable but clinically insignificant damage to the human central nervous system can be used to test the effectiveness of neuroprotective or neuroregenerative treatments, such as the administration of a test drug. Potentially, groups of patients desiring to undergo the LASIK procedure can be recruited as human test subjects for research on neurological drugs or other treatments. Procedures other than LASIK procedures also can be utilized to create minute but measurable damage to the nerve tissue of the human eye to test drugs for their neurological effects. Contrary to previous test procedures, the present methodology can be performed on human nervous tissue in vivo. An analyzer, such as the GDx® nerve fiber analyzer, provides a non-invasive way to accurately study the effects of a given treatment on nerve tissue.

In the preferred embodiment of carrying out the invention, a suction or vacuum is created on an external surface of an eye of a human. The vacuum should be sufficient to cause an intraocular pressure in the range from approximately 60 mm Hg to approximately 100 mm Hg as measured with a Mentor® pneumotonometer. More preferably, the intraocular pressure is in the range from approximately 70 mm Hg to approximately 90 mm Hg, and most preferably in the range from approximately 80 mm Hg to approximately 85 mm Hg. The vacuum is maintained on the eye for a period of approximately 20 seconds to approximately 120 seconds, more preferably from approximately 30 seconds to approximately 60 seconds, and most preferably approximately 40 seconds. The intraocular pressure and the duration should be selected such that only clinically insignificant damage to the nerve tissue results.

The method also includes administration of an appropriate treatment to the human subject either before and/or after application of the vacuum. The treatment may include administration of a variety of test drugs and substances considered for their potential neuroprotective or neuroregenerative characteristics. The drugs may be administered topically, ingested, injected or administered according to other suitable stratagems.

After a predetermined period or periods, the extent of loss to central nervous tissue, e.g. to the nerve fiber layer, is measured to determine the effect of the treatment. This effect is compared to a control subject. The control subject is a human subject who has undergone the same procedure but has been administered a placebo treatment, such as placebo drug. Comparison of statistically significant numbers of human test subjects to statistically significant numbers of human control subjects allows the researcher to draw conclusions about the effectiveness of a given treatment. The exact number of human test subjects and human control subjects as well as the testing protocol can vary but will typically be selected according to accepted scientific norms or standards.

As mentioned above, the use of eyes in testing the neuroprotective or neuroregenerative effects of a given treatment can facilitate the testing. Eyes are the only bilateral or duplicated manifestation of the human central nervous system, and this allows testing in which each human subject acts as both the human test subject and the human control subject, because one eye can be administered the test treatment while the other eye is administered the placebo treatment.

In an actual exemplary test to prove the present methodology, a patient undergoing LASIK in both eyes was administered a neuroprotective treatment in one eye and a placebo treatment in the other eye. Specifically, the patient was pretreated with brimonidine drops topically in one eye for four days, and then given brimonidine for ten days after the LASIK procedure. The patient's other eye was given artificial tears from an identical bottle over the same number of days. The patient was not aware of which solution was the brimonidine and which solution was the artificial tears.

During the LASIK procedure, the intraocular pressure in each eye was raised to between 80 and 90 mm Hg as measured with a Mentor® tonopen. The time of suction was maintained at 40 seconds in each eye. During this test, preoperative analysis of the nerve fiber layer of each eye was performed using a GDx® nerve fiber analyzer. At a predetermined time after the LASIK procedure, each eye was again analyzed by the GDx® nerve fiber analyzer to determine any loss of nerve fiber layer tissue.

In FIG. 1, the change in the nerve fiber layer of the patient's right eye is illustrated. The illustration is based on the nerve fiber layer information provided by the GDx® nerve fiber analyzer. Furthermore, the right eye is the eye that received the placebo drops of artificial tears.

In FIG. 1, block 10 illustrates the nerve fiber layer 12 of the right eye prior to the LASIK procedure. Block 14 provides a reference from which it may be determined whether a decrease in nerve fiber layer occurs. Block 16 provides an illustration of nerve fiber layer 12 approximately nine days after the LASIK procedure. A noticeable decrease in nerve fiber layer is apparent, as supported by the illustration in block 18. A clouded area 20 in block 18 represents the deviation or decrease in nerve fiber layer as compared to block 14. Area 20 in the actual GDx® nerve fiber analyzer results reflected a loss of 40 to 60 microns thickness in the upper and lower half of the patients nerve fiber layer in the untreated eye, while there was virtually no loss in the eye treated with brimonidine.

Figure 2:
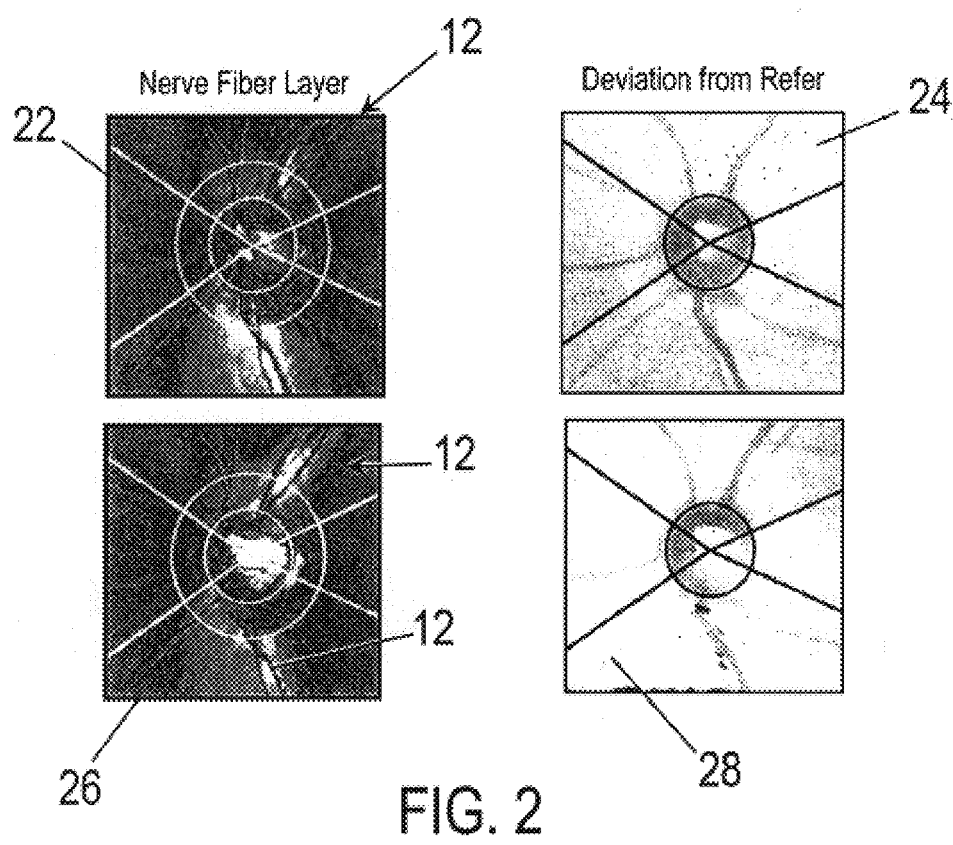
FIG. 2 is a figure similar to FIG. 1 illustrating analysis of the nerve fiber layer before and after application of a microkeratome to a human eye administered a neuroprotective drug.

In FIG. 2, a schematic representation of the nerve fiber analysis for the left eye is illustrated. The left eye received the above-described treatment of brimonidine. In block 22, nerve fiber layer 12 is represented as it appeared prior to the LASIK procedure. Block 24 again provides a reference to determine any deviation or change in the nerve fiber layer due to the raised intraocular pressure occurring during the LASIK procedure. As illustrated in blocks 26 and 28, there is very little change in the nerve fiber layer 12. In other words, the neuroprotective attributes of brimonidine was affirmed by this methodology.

To verify this methodology, a study was conducted on thirteen (13) patients in which LASIK was performed on one or both eyes of each patient. The intraocular eye pressure created during the LASIK procedures was between 80 and 90 mm Hg (as measured with a Mentor® tonopen) in all patients. The time of suction was maintained at 40 seconds in each eye tested, and preoperative and one month postoperative analysis of the nerve fiber layer of the eyes was performed using the GDx® nerve fiber analyzer.

In the largest subset of patients, one eye was pretreated with brimonidine drops topically for four days and given brimonidine drops for ten days after the LASIK procedure. The opposite eye was provided artificial tears from an identical bottle. The code telling which eye was treated with brimonidine and which eye was treated with the placebo was not known to the patient or any personnel involved in the automated nerve analysis. The results were reviewed one month after the LASIK procedure, and the results are represented graphically in FIG. 3.

In FIG. 3, horizontal axis 30 represents the patients subjected to the test, and vertical axis 32 represents loss of nerve fiber layer due to the rise in intraocular pressure during the LASIK procedure. In the graph, the decrease in nerve fiber layer for eyes treated with the neuroprotective brimonidine (brimonidine is sold under the trade Alphagan®) is represented by bars 34. On the other hand, the eyes treated with the placebo artificial tears are represented by the bars 36. As is apparent from the graph, the use of the neuroprotective resulted in substantially less change in the nerve fiber layer thickness relative to the control eyes that received a placebo before and after the LASIK procedure. The present methodology permits the testing of new drugs for their neuroprotective or neuroregenerative effects on human nervous tissue in vivo. This methodology potentially can accelerate the testing of such neurological drugs and advance the finding of cures for neurological disorders ranging from compression fractures of the human spine to strokes.

In testing a specific neuroprotective or neuroregenerative drug treatment, the substance or drug can be administered in a variety of ways. For example, the substance can be administered intravitreously, topically, intrathecally or orally, depending on the type of drug being tested. However, it has also been determined that a preferred method for administering neuroprotective agents during ophthalmological procedures, such as LASIK, is topical administration directly to the eye. For example, brimonidine and/or beta-adrenergic blocking agents, such as timolol, carteolo, levobunolol, betaxolol, atenolol, metoprolol, nadolol, pindolol, propanolol and labetalol, can be given topically. The topical application protects the neurotubules within the retinal ganglion cells and nerve fiber layer from damage to nerve tissue. This unique topical application is helpful in protecting or potentially regenerating nerve tissue at the human eye.

It will be understood that the foregoing description is of a preferred embodiment of this invention, and that the invention is not limited to the specific form shown. For example, a variety of intraocular pressures and durations of the pressure may be suitable for a given test procedure; the readily measurable but clinically insignificant damage to a human nerve fiber layer at a human eye can be the result of raised intraocular pressure during a LASIK procedure, another ophthalmological procedure or solely for the purpose of a given test procedure. Additionally, the exact design of the study and the number and characteristics of the human subjects involved may vary according to the treatment being tested and accepted test procedures and standards. These and other modifications may be made in the design and arrangement of the elements without departing from the scope of the invention as expressed in the appended claims.

What is claimed is:

1. A method for testing the neuroprotective or neuroregenerative effects of a substance on a human central nervous system without clinically significant damage to neural tissue, comprising:

creating a vacuum on an external surface of an eye of a human;

treating the human with a substance;

measuring the extent of loss to central nervous tissue to determine the effect of the substance; and comparing the extent of loss to a control.

2. The method as recited in claim 1, wherein treating comprises applying the substance topically.

3. The method as recited in claim 2, wherein applying comprises applying the substance to the eye.

4. The method as recited in claim 1, wherein said creating a vacuum includes engaging the eye with a suction ring.

5. The method as recited in claim 1, further comprising maintaining the vacuum for a period from approximately 20 seconds to approximately 120 seconds.

6. The method as recited in claim 1, further comprising maintaining the vacuum for a period from approximately 30 seconds to approximately 60 seconds.

7. The method as recited in claim 1, further comprising maintain the vacuum for a period of approximately 40 seconds.

8. The method as recited in claim 5, wherein said creating a vacuum includes creating a vacuum sufficient to cause an intraocular pressure in the range from approximately 60 mm Hg to approximately 100 mm Hg.

9. The method as recited in claim 5, wherein said creating a vacuum includes creating a vacuum sufficient to cause an intraocular pressure in the range from 70 mm Hg to 90 mm Hg.

10. The method as recited in claim 1, further comprising performing the method on a plurality of humans.

11. A method for testing neuroprotective or neuroregenerative effects of a treatment on nerve tissue of a human, comprising:

causing measurable damage to nerve tissue of a human;

treating the human; and measuring the depletion of nerve tissue following a designated period after the causing and the treating steps, wherein said causing measurable damage includes creating a vacuum on an external surface of an eye of the human.

12. The method as recited in claim 11, wherein the steps are performed in the order listed.

13. The method as recited in claim 11, wherein said treating the human includes treating a plurality of humans.

14. The method as recited in claim 11, further comprising comparing the depletion of nerve tissue to that of a control tissue.

15. The method as recited in claim 11, wherein said causing measurable damage comprises causing a reduction in a nerve fiber layer thickness proximate an eye.

16. The method as recited in claim 11, wherein creating includes creating an intraocular pressure of at least 60 mm Hg for a period of at least 20 seconds.

17. A method for testing neuroregenerative or neuroprotective effects on a human central nervous system, comprising:

producing measurable but clinically insignificant damage to a human central nervous system in a statistically significant number of human subjects;

producing measurable but clinically insignificant damage to a control human central nervous system in a statistically significant number of human control subjects;

treating the statistically significant number of human subjects with a test substance; and comparing human central nervous system damage in the statistically significant number of human subjects with the statistically significant number of human control subjects to determine the neuroprotective or neuroregenerative effects of the test substance, wherein producing measurable but clinically insignificant damage to a human central nervous system includes raising an intraocular pressure a sufficient amount over a sufficient duration in an eye of each of the human subjects.

18. The method as recited in claim 17, wherein producing measurable but clinically insignificant damage to a control human central nervous system includes raising an intraocular pressure a sufficient amount over a sufficient duration in a control eye of each of the human control subjects.

19. The method as recited in claim 18, further comprising utilizing each human subject as a human control subject.

* * * * *